United States Patent [19]
Cyprien et al.

[11] Patent Number: 5,723,018
[45] Date of Patent: Mar. 3, 1998

[54] SHOULDER-JOINT ENDOPROSTHESIS

[76] Inventors: Jean-Maxwell Cyprien, 3, route Antoine-Martin, 1234 Vessey, Switzerland; E. Bruno Gerber, 54, rue du Suchiez, 2006 Neuchâtel, Switzerland

[21] Appl. No.: 256,606
[22] PCT Filed: Nov. 16, 1993
[86] PCT No.: PCT/EP93/03218
 § 371 Date: May 19, 1995
 § 102(e) Date: May 19, 1995
[87] PCT Pub. No.: WO94/10941
 PCT Pub. Date: May 26, 1994

[30] Foreign Application Priority Data

Nov. 17, 1992 [DE] Germany .............. 42 38 832.5

[51] Int. Cl.$^6$ ...................................... A61F 2/40
[52] U.S. Cl. ............................................ 623/21
[58] Field of Search .................. 623/16, 18, 19, 623/22, 23

[56] References Cited

U.S. PATENT DOCUMENTS

| | | |
|---|---|---|
| 3,879,767 | 4/1975 | Stubstad . |
| 3,916,451 | 11/1975 | Bucchel et al. . |
| 4,550,340 | 10/1985 | Kinnett .......................... 623/18 |
| 4,846,840 | 7/1989 | Lederq et al. ................. 623/23 |
| 4,976,738 | 12/1990 | Frey et al. .................... 623/23 |
| 5,108,440 | 4/1992 | Grundei et al. ............... 623/19 |

FOREIGN PATENT DOCUMENTS

| | | |
|---|---|---|
| 0299889 | 1/1983 | European Pat. Off. . |
| 0322493 | 7/1989 | European Pat. Off. . |
| 0329854 | 8/1989 | European Pat. Off. . |
| 0342421 | 11/1989 | European Pat. Off. . |
| 2534587 | 2/1976 | Germany . |
| 2714387 | 11/1977 | Germany . |
| 3216111 | 11/1983 | Germany . |
| 1659042 | 6/1991 | U.S.S.R. ........................ 623/22 |

OTHER PUBLICATIONS

International Publication WO 89/07917 by Bioconcepts, Inc. entitled "Frangible Modular Joint Prosthesis".

*Primary Examiner*—David Isabella
*Attorney, Agent, or Firm*—Andrus, Sceales, Starke & Sawall

[57] ABSTRACT

The invention relates to a shoulder-joint endoprosthesis comprising a glenoid joint socket having a rearward part which has a porous structure for attachment to the shoulder blade. The socket is dished and substantially pear shaped. A humeral joint socket is fixed to the humerus by way of an intramedullary prosthesis stem. A joint ball is disposed between the glenoid joint socket and the humeral joint socket so as to be freely movable.

15 Claims, 5 Drawing Sheets

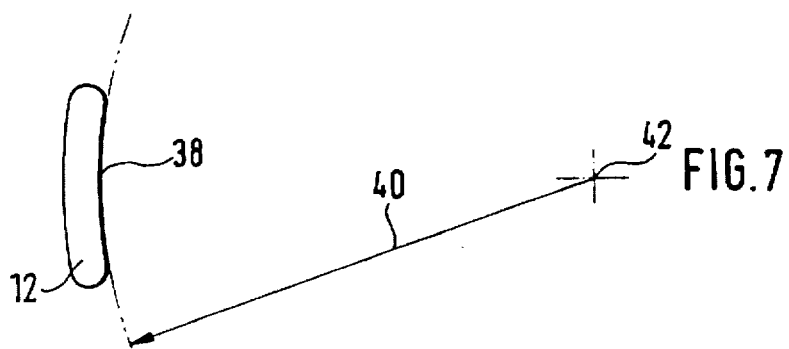
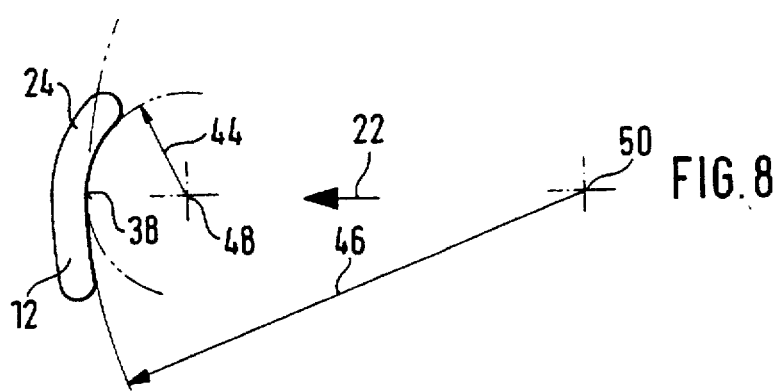
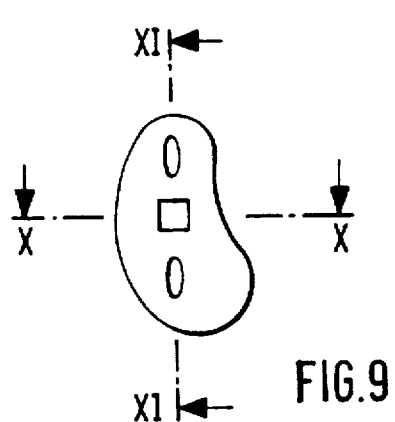
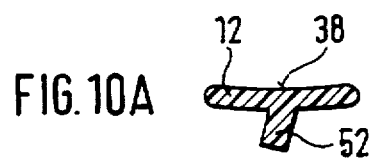
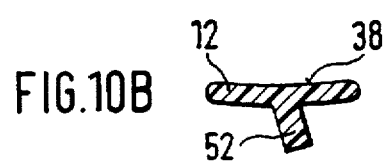
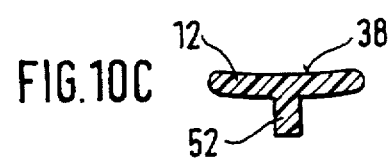
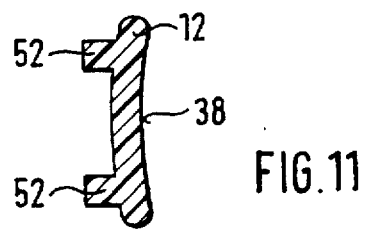

SHOULDER-JOINT ENDOPROSTHESIS

FIELD OF THE INVENTION

The present invention relates to a shoulder-joint endoprosthesis.

DESCRIPTION OF THE PRIOR ART

In nature the shoulder joint has the form of a ball joint, comprising on one side a shallow socket in the shoulder blade and on the other side, connected to the socket, a large head at the end of the humerus. To make the shoulder joint highly mobile, the joint capsule is wide and the ligaments are weakly developed. The forces that arise are thus transmitted into the humerus by way of the outer layers of the bone etc., with no stepwise change in force. The shoulder joint is held together and prevented from dislocation exclusively by muscles. For example, the tendon of origin of the long head of the biceps itself passes through the shoulder joint and under pressure becomes displaced against the humerus.

In the past, in cases of destruction or severe structural alteration of the shoulder joint or glenohumeral joint, i.e. the joint between the shoulder blade and the upper bone of the arm, a great variety of complete joint replacement systems has been proposed for implantation in humans. For example, in German patent Specification DE 32 16 111 C2 a shoulder-joint endoprosthesis is described that comprises a humerus shaft to be anchored in the humerus and a scapula shaft to be anchored in the scapula, each with a round head at its exposed end. The two heads in turn are functionally engaged with one another by way of a ball joint in the form of a spherical, rotatable bearing element. There is a very similar arrangement in the shoulder-joint endoprosthesis described in German Patent Specification DE 27 14 387 C3. All these shoulder-joint endoprostheses have proved to be clearly disadvantageous with respect both to their elaborate construction and to the transmission of forces. In particular, the forces are transmitted by way of the ball heads and the associated shafts directly onto the shoulder blade or the humerus, or directly into the shoulder blade or the humerus. This results in an enormous stepwise change in force and hence a stepwise moment of force, which applies a high load to the shoulder blade and/or the humerus. Not uncommonly a relative movement is induced between the shoulder blade and the scapula shaft on one side and/or the humerus and the humerus shaft on the other, which in turn causes the durability of the whole shoulder-joint endoprosthesis to be low and can also delay the process of osteointegration between the shoulder blade or humerus and the foreign body.

The present invention is directed to the problem of providing a shoulder-joint endoprosthesis that is simple in construction, that has a favorable transmission of forces, and that is highly compatible with the bone.

SUMMARY OF THE INVENTION

According to the present invention, there is provided a shoulder-joint endoprosthesis comprising a glenoid joint socket for attachment to a shoulder blade, a humeral joint socket with an intramedullary prosthesis stem, by means of which it can be attached to a humerus and a joint ball for disposition between the glenoid joint socket and the humeral joint socket so that it is freely movable.

The artificial glenoid joint socket has a rearward part for attachment to the shoulder blade. With this construction, it is possible to replace, for example, a completely shattered glenoid joint. Further, within the scope of the invention, the rearward part or the like is made with a pore diameter greater than or equal to 100 μm to promote ingrowth of the bone of the shoulder blade. This improves the stability of the glenoid joint socket within the shoulder blade.

Although the design of the shoulder-joint endoprosthesis in accordance with the invention represents a departure from nature in that the shoulder-joint endoprosthesis consists of three parts, namely a glenoid joint socket, a humeral joint socket and freely movable central joint ball disposed between the glenoid joint socket and the humeral joint socket, this arrangement provides additional degrees of freedom so that especially great mobility is achieved. As a result, force is conducted into the shoulder blade or into the humerus with no stepwise changes. Shear loads and torques acting on the individual components of the shoulder-joint endoprosthesis in accordance with the invention are greatly reduced owing to the arrangement in accordance with the invention, which enables rolling as well as sliding as well as translatory movement of the joint ball between the glenoid joint socket and the humeral joint socket. This in turn results in much less relative movement between the scapular implant and the shoulder blade, and also between the humeral implant and the humerus. A so-called foreign-body effect is not altogether excluded by the shoulder-joint endoprosthesis in accordance with the invention, but it is at least profoundly reduced.

Furthermore, the shoulder-joint endoprosthesis in accordance with the invention has a particularly simple structure, because it is not necessary for the individual components, i.e. the glenoid joint socket, the humeral joint socket and the freely movable joint ball disposed between the glenoid joint socket and the humeral joint socket, to be fixed with respect to one another.

Thus the shoulder-joint endoprosthesis, like the natural shoulder joint, is held in place and secured only by muscles and tendons. Accordingly, the joint ball is stabilized in the back region of the shoulder blade by the supraspinous and infraspinous muscles and retained in the front region by the subscapular muscle. Finally, the joint ball is held together in the upper region by a tendon plate, the so-called rotator cuff. Additional structures serving to hold together the shoulder-joint endoprosthesis in accordance with the invention are the fibrous joint capsule as well as other muscles and soft parts (so-called hammock effect). Finally, again as in nature, within and around the shoulder-joint endoprosthesis a vacuum develops that keeps the glenoid joint socket, the humeral joint socket and the joint ball between them securely together.

An especially advantageous feature of the shoulder-joint endoprosthesis in accordance with the invention, moreover, is that it can be employed for a patient in whom the glenoid joint socket is not damaged, as can happen for instance in the case of humerus fractures that destroy the head of the bone or in aseptic necrosis. In this case what is implanted as shoulder-joint endoprosthesis in accordance with the invention is merely the humeral joint socket, attached to the humerus by way of an intramedullary prosthesis stem, and the joint ball, under the condition that there is no accompanying paralysis of the shoulder girdle, the deltoid muscle or the rotator-cuff muscles.

Preferably, the glenoid joint socket is made of polyethylene or material of the type used for sliding bearings, which is applied to the rearward part to form the glenoid joint socket. Preferably also, the rearward part is made of metal or a material with similar properties to metal such as titanium or a titanium alloy. This construction ensures the required compatibility between the glenoid joint socket and the bone material, in this case the shoulder blade. Furthermore, by constructing the glenoid joint socket of polyethylene or a similar material of the kind used for sliding bearings, an additional reduction of shear force and torque is achieved, so that the bone material of the shoulder blade grows more rapidly into the glenoid joint socket.

In order to further reduce shear forces and torques, which not uncommonly cause the patient appreciable pain, the glenoid joint socket is preferably dished and substantially pear-shaped, an upper part of the glenoid joint socket having a smaller radius of curvature than a lower part of the glenoid joint socket. Such a non-spheroid shape of the glenoid joint socket permits additional degrees of freedom, which enable a substantially step-free transmission of force into the bone.

The glenoid joint socket in addition preferably includes an overhanging rim for a neutral just as for a left or a right glenoid joint socket. This allows high flexibility for the implantation of the glenoid joint socket in retroversion with respect to the plane of the shoulder blade.

Preferably also the humeral joint socket is made of polyethylene or a material of the type used for sliding bearings, which is applied to the prosthesis stem, which is made of metal or a material with similar properties to metal, such as titanium or a titanium alloy, to ensure a high compatibility between the humeral joint socket with its prosthesis stem and the bone material of the humerus.

The prosthesis stem is preferably fixed in a marrow cavity of a humerus with a plateau angle α in the range 50°–60° inclusive. The whole humeral joint socket can thus be implanted in retrotorsion with respect to the plane of the humeral condyle.

Preferably also, the humeral joint socket has a large inside radius, matched with that of the joint ball. This guarantees high mobility of the joint ball for rolling, sliding and also translatory movement in or at the humeral joint socket.

In order to secure greater retention of the joint ball between the glenoid joint socket and the humeral joint socket in the direction of the lower end of the body, the humeral joint socket preferably comprises a projection or the like that is positioned caudally. Such a projection enables better centering of the joint ball between the glenoid joint socket and the humeral joint socket when the arm is extended to the side, as well as providing extra support of the joint ball when the arm is hanging freely down.

Preferably also, the joint ball is made of metal or the like in order to advantageously increase tissue compatibility, especially with the fibrous joint capsule that surrounds it. For weight reduction, the joint ball is preferably constructed as a hollow sphere.

Preferably also, the size of the joint ball is selected depending on joint the tension and the interior volume of the rotator cuff in each individual case. This enables the surgeon to respond flexibly to the conditions encountered in the shoulder-joint region during the actual operation, by the rapid, uncomplicated procedure of selecting a joint ball with diameter suited to the individual. Accordingly, the reconstruction and the determination of the interior volume in the rotator cuff, simultaneously taking account of the joint tension, can be carried out with extreme reliability.

Preferably also, the glenoid joint socket is snap fitted to the rearward part by way of a catch, snap or similar device. This has the advantage that on one hand connection of the glenoid joint socket to the rearward part can be carried out very simply, while on the other hand flexibility is inexpensively achieved by attaching joint sockets of various shapes, individually suited to the demands of the particular case, to a uniformly shaped rearward part.

Preferred embodiments of the accompanying invention will now be described by way of example with reference to the drawings.

BRIEF DESCRIPTION OF THE DRAWINGS

FIG. 7 is a schematic side view of an embodiment of the glenoid joint socket shown to FIG. 1;

FIG. 8 is a schematic view of a modified glenoid joint socket shown to FIG. 7;

FIG. 9 is a plan view of the direction of arrow 22 of glenoid joint socket shown in FIGS. 2 and 8;

FIGS. 10A, 10B and 10C are cross sections of three embodiments of glenoid joint sockets along the line X—X in FIG. 9;

FIG. 11 is a longitudinal section of the glenoid joint socket along the line XI—XI in FIG. 9;

DESCRIPTION OF THE PREFERRED EMBODIMENT

Figure 1:
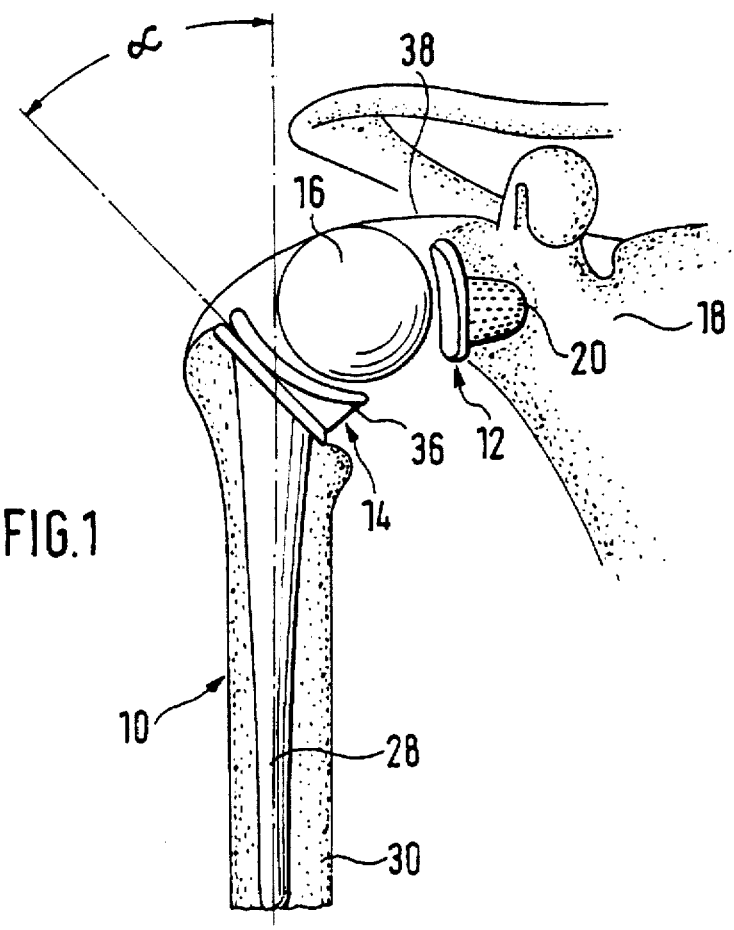
FIG. 1 is a side view of an first embodiment of a shoulder-joint endoprosthesis according to the invention.

In FIG. 1 a first embodiment of a shoulder-joint endoprosthesis 10 is shown schematically. The shoulder-joint endoprosthesis 10 comprises a glenoid joint socket 12, a humeral joint socket 14 and a joint ball 16 so disposed between the glenoid joint socket 12 and the humeral joint socket 14 as to be freely movable.

The glenoid joint socket 12 is attached to a shoulder blade 18, by means of a rearward part 20. The glenoid joint socket 12 consists of polyethylene or a similar material of the kind used in sliding bearings, which is applied to the rearward part 20 of the glenoid joint socket 12 or is taken up by the latter. The rearward part 20 itself is made of metal or the like, in particular titanium or a titanium alloy, which is especially compatible with the bone material of the shoulder blade 18.

Figure 2:
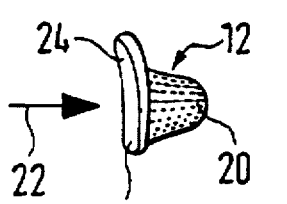
FIG. 2 is a side view of the glenoid joint socket shown in FIG. 1.

The rearward part 20 is, as indicated in FIG. 2, porous or the like and as shown by the portion of the upper and lower parts extending from the part 20 for integration with the bone of the shoulder blade. In particular, the rearward part 20 has a porous structure with a pore diameter greater than or equal to 100 μm. By this means the rearward part 20 and, together with it, the glenoid joint socket 12 it bears, are held securely in the bone of the shoulder blade 18, which in time grows into the individual pores of the rearward part 20.

The glenoid joint socket 12 is substantially dish-shaped and in plan view, as indicated by arrow 22 in FIG. 2, pear-shaped. Here, the upper part 24 of the glenoid joint socket 12 has a smaller radius of curvature than the lower part 26 of the glenoid joint socket 12. Furthermore, the glenoid joint socket 12 is provided with an overhanging rim or lip, or the like.

Figure 3:
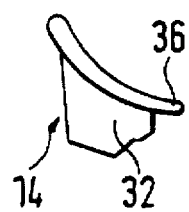
FIG. 3 is a side view of the humeral joint socket shown in FIG. 1.
Figure 4:
FIG. 4 is a side view of the intramedullary prosthesis stem shown in FIG. 1.

The humeral joint socket 14 shown in FIGS. 1 and 3 can be fixed to the humerus 30 by way of an intramedullary prosthesis stem 28. The humeral joint socket 14 is also made of polyethylene or a similar material of the kind used in sliding bearings, which is applied to the prosthesis stem 28, for example by way of a rearward part 32 that can be inserted into and fixed within an opening 34 of the prosthesis stem 28. The prosthesis stem 28 itself consists of metal or the like, in particular of titanium or a titanium alloy, which is especially compatible with the bone material of the humerus 30 that surrounds the prosthesis stem 28.

As indicated in FIG. 1, the prosthesis stem 28 is fixed in the marrow cavity with a plateau angle α of preferably ca. 50° to 60° between the center line of the stem and a line through the humeral joint socket.

To increase the degrees of freedom, the humeral joint socket 14 is constructed with a large inside radius, preferably matched to the joint ball 16. In addition, the humeral joint socket 14 according to FIGS. 1 and 3 includes a projection 36 or the like, located caudally or toward the lower end of the body. The projection 36 thus serves advantageously both to center the joint ball 16 when the humerus 30 is held out to the side, in which case the joint ball 16 is simultaneously kept in place, for example, by the subscapular muscle (not shown), and also to provide extra support for the joint ball 16 when the humerus 30 is hanging freely down as shown in FIG. 1.

The joint ball 16 itself is made of metal or similar material that is compatible with the fibrous joint capsule enclosing the joint ball 16. Preferably the joint ball 16 has the form of a hollow sphere.

Figure 5A:
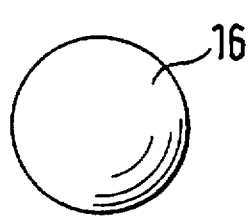
FIGS. 5A, 5B and 5C are side views of the joint ball shown in FIG. 1 and other joint balls with a larger and a smaller respectively.
Figure 5B:
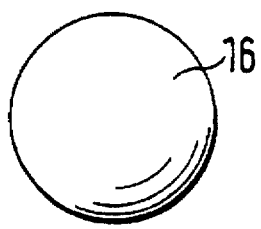
Figure 5C:
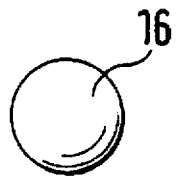

As shown in FIGS. 5A to 5C, the joint ball 16 is variable in size, so that it can be selected according to the joint tension and the interior volume of the rotator cuff in the individual case, which can often be determined only by the surgeon during the operation.

The design of the shoulder-joint endoprosthesis 10 in accordance with the invention is such as to guarantee high mobility with a mobile center of rotation and to enable sufficient reconstruction of the rotation cuff with allowance for an adequate joint tension, with a simultaneous reduction of the shear forces and torques acting on the glenoid joint socket 12 fixed in the bone of the shoulder blade 18 and/or on the humeral joint socket 14 with its humeral prosthesis stem 28 fixed in the humerus 30.

Figure 6:
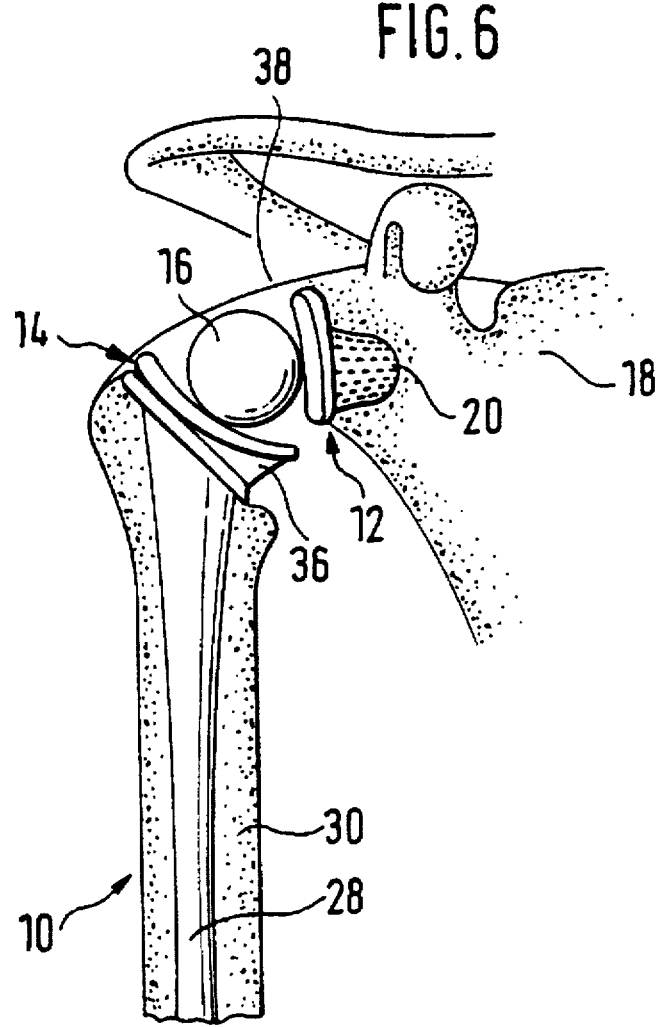
FIG. 6 is a side view of a second embodiment of a shoulder-joint endoprosthesis according to the invention having a joint ball as shown in FIG. 5C.

A further embodiment of a shoulder-joint endoprosthesis 10 in accordance with the invention is shown in FIG. 6. This second embodiment of a shoulder-joint endoprosthesis 10 in accordance with the invention as shown in FIG. 6 differs from that according to FIG. 1 only in having a joint ball 16 of smaller diameter. In the drawings identical parts are indicated by identical reference numerals.

The size of the joint ball 16 is determined, for example, by the extent of the damage to the rotator cuff, indicated by reference numeral 38. Accordingly, the joint ball 16 has small diameter as in FIG. 6 in case of a major defect in the rotator cuff 38, whereas the joint ball 16 has large diameter as in FIG. 1 in case of a small tear in the rotator cuff 38. The other muscles that ensure stabilization of the shoulder joint, as well as of the shoulder-joint endoprosthesis 10 in accordance with the invention as in FIGS. 1 and 6, are not shown in the figures.

The invention is not limited to the illustrated embodiments. It would also be conceivable for example, in the case of a patient with only slight damage to the natural glenoid joint socket, merely to fix a humeral joint socket 14 with associated intramedullary prosthesis stem 28 to the humerus 30 and to insert a joint ball 16 of suitable size between the natural glenoid joint socket and the implanted humeral joint socket 28. In particular, such a procedure is applicable for certain fractures of the humerus in which the head is destroyed or for aseptic necrosis.

In the embodiment with an approximately dish-shaped glenoid joint socket 12, as shown in FIG. 7, the inner surface 38 of the glenoid joint socket 12 is formed with only a single radius of curvature 40 with a center of curvature as indicated at 42. In contrast, the inner surface 38 of the glenoid joint socket 12 as shown in FIG. 8 is formed by a total of two different radii 44, 46, with the centers of curvature 48, 50. As shown in FIG. 8, the upper part 24 of the glenoid joint socket 12 has the smaller radius 44, and the lower part 26 of the glenoid joint socket 12 has the larger radius 46.

In FIGS. 9 to 11 various embodiments of the glenoid joint socket 12 are illustrated, that in FIG. 10A being intended for a left shoulder and that in FIG. 10B for a right shoulder. In FIG. 10C a glenoid joint socket 12 is shown as a neutral element. The backward-extending pegs 52 to fix the glenoid joint socket 12 to the rearward part 20 can be perforated (not shown) to increase the stability of the fixation.

Figure 12:
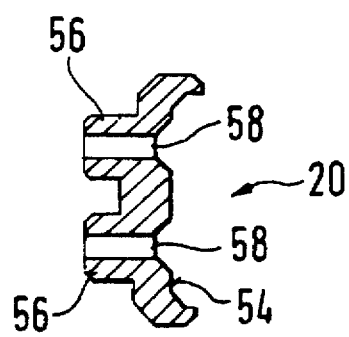
FIG. 12 is a longitudinal section through a first embodiment of a rearward part.
Figure 13:
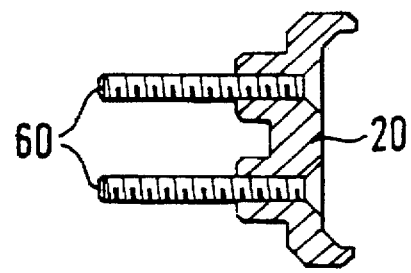
FIG. 13 is a longitudinal section through the the rearward part shown to FIG. 12 with fixing screws.

The rearward part 20 in FIG. 12 is dish-shaped on its forward surface 54 in order to receive a glenoid joint socket 12. Furthermore, there are formed integral with the rearward part 20 two projections 56 with bores 58 extending backward, approximately perpendicular to the forward surface 54 of the rearward part 20. The rearward part 20 according to FIG. 13 is fastened to the bone material by means of screws 60, each of which extends through the bore 58 in the corresponding projection 56.

Figure 14:
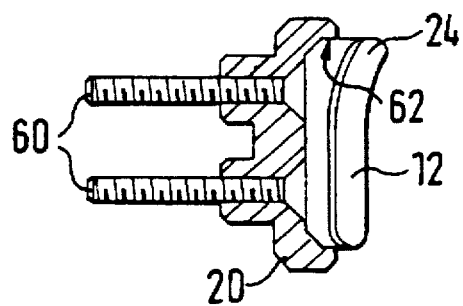
FIG. 14 is a longitudinal section through the rearward part shown in FIG. 13 when connected to a glenoid joint socket as shown in to FIG. 7.
Figure 15:
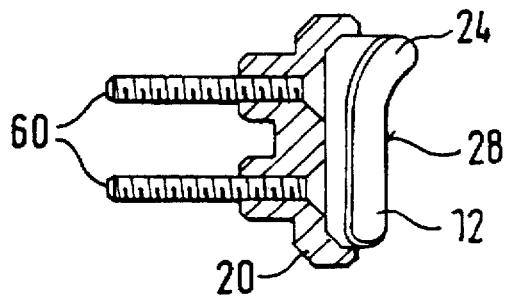
FIG. 15 is a longitudinal section through the rearward part shown in FIG. 13 when connected to a glenoid joint socket as shown in FIG. 8.

According to FIGS. 14 and 15, after the rearward part 20 has been fixed to the bone material by placement of the screws 60, the individually selected glenoid joint socket 12 can be set onto the forward surface 64 of the rearward part 20 where it is then snap-filled into position or received by the catching or snapping action of a catch, snap or similar device 62. The two embodiments according to FIGS. 14 and 15 differ from one another only in the shape of the inner surface 38, with the radii of curvature 40 and 44, 46, respectively.

Figure 16:
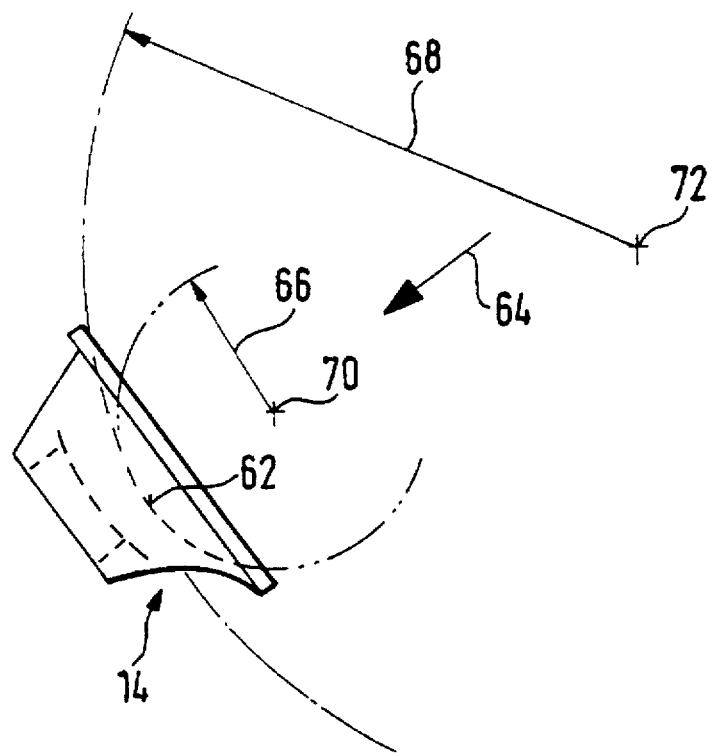
FIG. 16 is an enlarged schematic side view of the humeral joint socket shown in FIG. 3.
Figure 17:
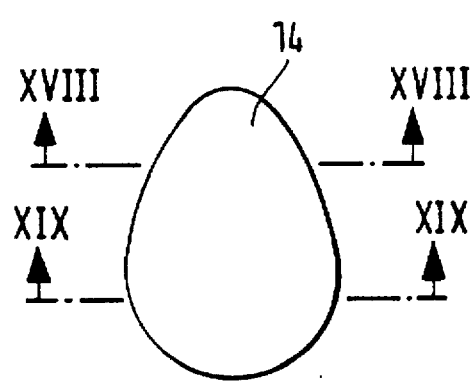
FIG. 17 is a plan view in the direction of arrow 64 of the humeral joint socket shown in FIG. 16.
Figure 18:
FIG. 18 is a cross section through the humeral joint socket along the line XVIII—XVIII in FIG. 17.
Figure 19:
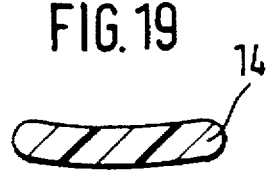
FIG. 19 is a cross section through the humeral joint socket along the line XIX—XIX in FIG. 17.

The embodiment of the humeral joint socket 14 shown in FIG. 16 likewise has an inner surface 62 that is dished and, in plan view in the direction of arrow 64, pear-shaped. The inner surface 62 is likewise formed by two different-sized radii of curvature 66, 68 with the respective centers of curvature 70, 72. As is shown in FIG. 17, the humeral joint socket 14 is likewise approximately pear-shaped.

What is claimed is:

1. A shoulder-joint endoprosthesis comprising:
   a glenoid joint socket having a rearward part for attachment to a shoulder blade,
   a humeral joint socket with an intramedullary prosthesis stem by means of which it can be attached to a humerus,
   a joint ball socket located between the glenoid joint socket and the humeral joint socket and being freely movable therein,
   said glenoid joint socket being dished and substantially pear-shaped, said glenoid joint socket having a lower part and art upper part, and said upper part having a smaller radius of curvature than said lower part of said glenoid joint socket.

2. A shoulder-joint endoprosthesis comprising:
   a glenoid joint socket having a rearward part for attachment to a shoulder blade, said rearward part including a porous structure for integration with the bone of the shoulder blade,
   a humeral joint socket with an intramedullary prosthesis stem by means of which it can be attached to a humerus,
   a joint ball located between the glenoid joint socket and the humeral joint socket and being freely movable therein,
   said glenoid joint socket being dished and substantially pear-shaped, said glenoid joint socket has a lower part and an upper part, and said upper part having a smaller radius of curvature than said lower part of said glenoid joint socket.

3. The shoulder-joint endoprosthesis of claim 2, wherein the material of the rearward part of the glenoid joint socket is selected from the group consisting of polyethylene and materials similar to polyethylene and used in sliding bearings.

4. The shoulder-joint endoprosthesis of claim 2 wherein the material of the rearward part is selected from the group consisting of titanium or titanium alloy.

5. The shoulder-joint endoprosthesis of claim 2, wherein said porous structures includes a plurality of pores having a diameter of at least equal to 100 µm.

6. The shoulder-joint endoprosthesis of claim 2, wherein the glenoid joint socket includes an overhanging rim.

7. The shoulder-joint endoprosthesis of claim 2, wherein the humeral joint socket is of a material selected from polyethylene and material similar to polyethylene and used for sliding bearings.

8. The shoulder-joint endoprosthesis of claim 2, wherein the prosthesis stem is of a material selected from titanium and a titanium alloy.

9. The shoulder-joint endoprosthesis of claim 2, wherein the prosthesis stem can be fixed in a marrow cavity of a humerus with a plateau angle $\alpha$ in the range of 50° to 60° inclusive between the centerline of the stem and a line through the humeral joint socket.

10. The shoulder-joint endoprosthesis of claim 5, wherein the humeral joint socket has an inside radius matched with that of the joint ball.

11. The shoulder-joint endoprosthesis of claim 2, wherein the humeral joint socket includes a body and a projection positioned caudally toward the lower end of said body.

12. (The shoulder-joint endoprosthesis of claim 2, wherein the joint ball is made of metal.

13. The shoulder-joint endoprosthesis of claim 2, wherein the joint ball comprises a hollow sphere.

14. The shoulder-joint endoprosthesis of claim 2, wherein said shoulder joint has a known joint tension and a rotator cuff of a known interior volume and including the joint ball having a size related to said joint and said interior volume of said rotator cuff.

15. The shoulder-joint endoprosthesis of claim 2, wherein said glenoid joint socket includes a socket part separated from said rearward part, and including a snap-fit connection between said socket part and said rearward part.

* * * * *

UNITED STATES PATENT AND TRADEMARK OFFICE
CERTIFICATE OF CORRECTION

PATENT NO. : 5,723,018

DATED : March 3, 1998

INVENTOR(S) : JEAN-MAXWELL CYPRIEN

It is certified that error appears in the above-identified patent and that said Letters Patent is hereby corrected as shown below:

Claim 1, column 7, line 18, delete "art" and insert -- an --; Claim 12, column 8, line 27, before "The" delete "(" (Parenthesis).

Signed and Sealed this

Twenty-eighth Day of July, 1998

Attest:

BRUCE LEHMAN

*Attesting Officer*     *Commissioner of Patents and Trademarks*